US006259097B1

(12) United States Patent
Shao et al.

(10) Patent No.: US 6,259,097 B1
(45) Date of Patent: Jul. 10, 2001

(54) USE OF TRANSMISSION PRE-SCAN OF AN OBJECT TO BE IMAGED TO DETERMINE DURATION OF TRANSMISSION SCAN

(75) Inventors: Lingxiong Shao, San Jose; Jinghan Ye, Fremont; Soo Kuen Hom, Milpitas, all of CA (US)

(73) Assignee: ADAC Laboratories, Milpitas, CA (US)

( * ) Notice: Subject to any disclaimer, the term of this patent is extended or adjusted under 35 U.S.C. 154(b) by 0 days.

(21) Appl. No.: 09/322,295

(22) Filed: May 28, 1999

(51) Int. Cl.[7] ................................................... G01T 1/20
(52) U.S. Cl. ........................................ 250/363.04; 378/145
(58) Field of Search ........................ 250/363.04; 378/145, 378/146, 108, 4, 16, 57

(56) References Cited

U.S. PATENT DOCUMENTS

| 4,012,636 | * | 3/1977 | Engdahl et al. | 250/363 |
| 5,182,764 | * | 1/1993 | Peschmann et al. | 378/57 |
| 5,608,221 | * | 3/1997 | Bertelsen et al. | 250/363.03 |
| 5,612,985 | * | 3/1997 | Toki et al. | 378/4 |
| 5,629,971 | | 5/1997 | Jones et al. . | |
| 5,682,036 | | 10/1997 | Hines et al. . | |
| 5,834,779 | * | 11/1998 | Shao et al. | 250/363.03 |

OTHER PUBLICATIONS

Tan, Patrick et al., "A Scanning Line Source for Simultaneous Emission and Transmission Measurements in SPECT", *The Journal of Nuclear Medicine*, vol. 34, No. 10, Oct. 1993, pp. 1752–1760.

* cited by examiner

*Primary Examiner*—Robert H. Kim
*Assistant Examiner*—Irakli Kiknadze
(74) *Attorney, Agent, or Firm*—Jordan M. Becker (57) ABSTRACT

A transmission pre-scan of a patient is used in a nuclear medicine imaging system to determine the duration of a subsequent transmission scan of the patient. The transmission scan is for acquiring an attenuation map of the patient to correct emission data of the patient for non-uniform attenuation. As a result, the patient's exposure to radiation during the transmission scan is not excessive, yet transmission image quality is maintained. A radiation transmission source and a radiation detector are operated to perform the transmission pre-scan of the object, during which the transmission source remains in a fixed position. Downscatter correction is applied to correct the transmission pre-scan data for emission contamination. Count values from the pre-scan data are integrated axially. A water-equivalent cross-section value of the patient is then determined based on data acquired from the transmission pre-scan, and the duration of the transmission scan is computed based on the water-equivalent cross-section value.

42 Claims, 8 Drawing Sheets

USE OF TRANSMISSION PRE-SCAN OF AN OBJECT TO BE IMAGED TO DETERMINE DURATION OF TRANSMISSION SCAN

FIELD OF THE INVENTION

The present invention pertains to nuclear medicine imaging systems. More particularly, the present invention relates to a technique for determining the duration of a transmission scan for acquiring an attenuation map of a patient.

BACKGROUND OF THE INVENTION

In the field of nuclear medicine, a patient is injected with a radiopharmaceutical substance, and images of internal structures or functions of the patient's body are generated by an imaging system that detects radiation emitted by the substance. The imaging system typically uses one or more scintillator-based detectors to detect the radiation. A computer system controls the detectors to acquire data based on the detected radiation and processes the data, using a technique known as tomography to generate the images. Nuclear medicine imaging techniques include Single-Photon Emission Computed Tomography (SPECT) and Positron Emission Tomography (PET), or "coincidence" imaging.

One factor that can affect image quality in nuclear medicine imaging systems is the non-uniform attenuation of radiation within the body. Non-uniform attenuation tends to distort and introduce artifacts in images generated by the imaging system. The effects of attenuation can be especially significant in cardiac studies due to attenuation caused by the thorax. Most modern nuclear medicine systems provide correction for non-uniform attenuation. One common technique is to perform a transmission scan of the patient either before or concurrently with the emission scan. During the transmission scan, radiation is transmitted through the patient's body from an external radiation source to one or more detectors of the imaging system. The data acquired based on the transmission scan represents an "attenuation map" of the patient, which can be used to correct the emission data for the effects of attenuation.

An undesirable consequence of the above-mentioned attenuation correction technique is that the patient is exposed to additional radiation. Consequently, it is desirable to limit the amount of this additional radiation. One way of doing this is to limit the duration of the transmission scan. However, a certain minimum amount of transmission radiation must be used to enable the detectors to acquire enough data to form a usable attenuation map. One possible approach is to use the same amount of transmission radiation regardless of the size and shape of the patient. However, with such an approach, patients with very small bodies would tend to be exposed to more transmission radiation then is necessary. Similarly, a transmission scan of a very large patient would tend to yield insufficient transmission data.

With certain prior art nuclear medicine imaging systems, a medical technician decides what the duration of the transmission scan should be, based on the size and shape of the patient. This decision may be made on the basis of recommendations from the manufacturer of the imaging system. However, because the decision is based on human judgment and approximations, it is inherently subject to error. U.S. Pat. No. 5,629,971 of Jones et al., which is assigned to the assignee of the present invention, describes a technique for computing a desired duration of the transmission scan for each patient, based on results of a brief transmission "pre-scan". However, the described technique, which requires complete motion of the radiation line source across the field of view of the detector, tends to expose the patient to more radiation during the transmission pre-scan than is desirable. In addition, the described technique fails to take into consideration the effects of emission contamination in the transmission pre-scan. Emission contamination may result when the transmission scan is performed after injection of the radiopharmaceutical, and the emission and transmission energy ranges overlap, as is often the case.

SUMMARY OF THE INVENTION

The present invention includes a method and apparatus for using a transmission pre-scan of an object to be imaged to determine the duration of a transmission scan of the object. As a result, the object's exposure to radiation during the transmission scan is not excessive, yet transmission image quality is maintained. Axial integration of count values resulting from the transmission pre-scan allows the pre-scan to be performed with the source in a fixed axial position, to further reduce pre-scan radiation exposure. A correction may be applied to correct the transmission pre-scan data for emission contamination.

In one embodiment, water-equivalent cross-section value of the object is determined based on data acquired from the transmission pre-scan. The duration of the transmission scan is then computed based on the water-equivalent cross-section value.

In another embodiment, the transmission pre-scan data includes multiple count values, each count value associated with one of a plurality of positions along a first axis. A subset of the count values is selected based on the count values, and a value corresponding to an average of the subset of the count values is computed. The duration of the transmission scan is then computed based on the value and the duration of the transmission pre-scan.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A method and apparatus are described for performing a transmission pre-scan of a patient using a nuclear medicine imaging system, to determine the duration of a subsequent transmission scan of the patient. The transmission scan is for acquiring an attenuation map of the patient to correct emission data of the patient for non-uniform attenuation. As a result, the patient's exposure to radiation during the transmission scan is not excessive, yet transmission data quality is maintained.

As will be described in greater detail below, a radiation transmission source and a radiation detector are operated to perform the transmission pre-scan of the object. Downscatter correction is applied to correct the transmission pre-scan data for emission contamination. Count values from the pre-scan data are integrated axially to allow the pre-scan to be performed with the radiation source in a fixed axial position. A water-equivalent cross-section value of the patient is then determined based on data acquired from the transmission pre-scan, and the duration of the transmission scan is computed based on the water-equivalent cross-section value.

Figure 1:
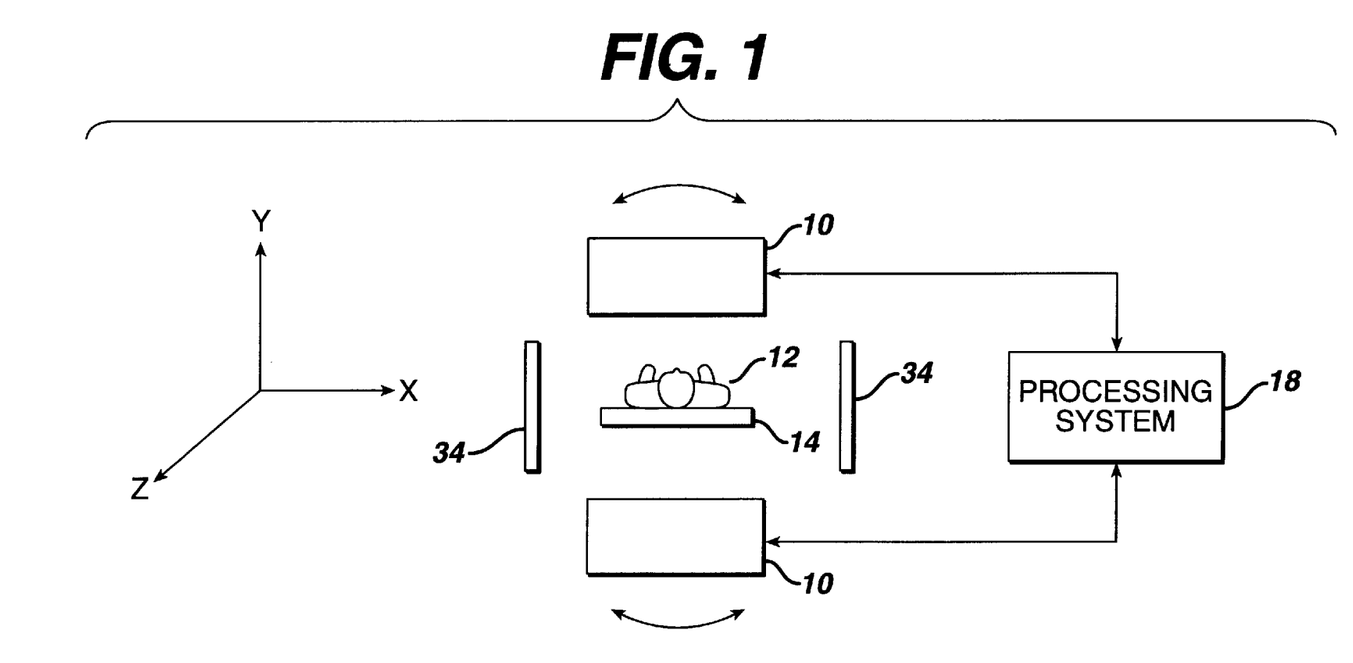
FIG. 1 illustrates the nuclear medicine imaging system in which the present invention can be implemented.

FIG. 1 is a block diagram of a dual-detector nuclear medicine imaging system, which is capable of single-photon (SPECT) imaging, coincidence (PET) imaging, or both. The system of FIG. 1 includes a processing system 18 coupled to two gamma camera detectors 10. Each of the detectors 10 includes a scintillator, such as a NaI(Tl) crystal. Each of the detectors 10 includes components for detecting scintillation events in response to gamma radiation and for providing data representing detected events to the processing system 18. The imaging system also includes a pair of transmission radiation line sources 34, for performing transmission scans.

The detectors 10 and the line sources 34 may be supported by a gantry (not shown). The gantry is capable of rotating the detectors 10 (individually or in unison) and the line sources 34 about an axis of rotation passing through the patient perpendicular to the x-y plane (parallel to the z axis). The gantry is also capable of moving the detectors 10 and the line sources 34 in translation along the z axis. The line sources 34 also can be moved in translation along the z axis relative to the detectors 10.

During an imaging session, a patient 12 rests on a table 14 positioned between the detectors 10. In FIG. 1, the detectors 10 are shown in a 180-degree orientation relative to each other about the axis of rotation, as is appropriate for either coincidence imaging or SPECT imaging.

The processing system 18 generally controls the operation of the gantry and the detectors, receives data acquired by the detectors 10, processes the data, and reconstructs images of the patient based on the data. The processing system 18 may be, or may include, for example, one or more of: a conventional computer system, such as a personal computer (PC), a workstation, a single-board computer, or a combination of such devices. Note that in alternative embodiments, however, some of the above-mentioned functions of the processing system 18, or aspects thereof, may instead be implemented within the detectors 10, the gantry, or in other distinct modules. Thus, processing system 18 may be embodied as two or more physically distinct processing systems.

Figure 2:
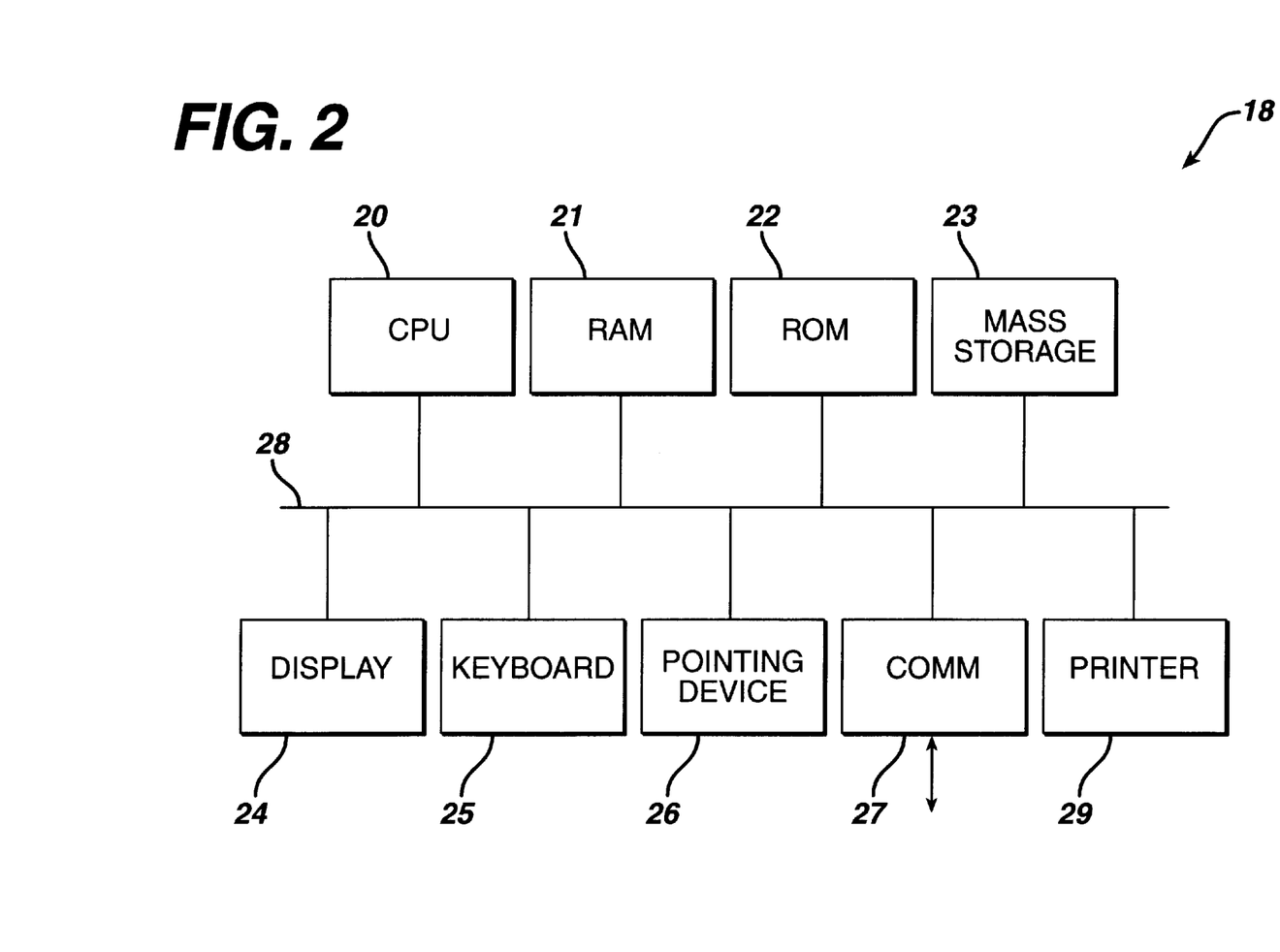
FIG. 2 is a high-level block diagram of the processing system of FIG. 1.

FIG. 2 illustrates a block diagram of the processing system 18 according to one embodiment. As illustrated, the processing system 18 includes a central processing unit (CPU) 20, random access memory (RAM) 21, read-only memory (ROM) 22, and a mass storage device 23, each coupled to a bus system 28. The bus system 28 may represent multiple physical buses coupled together by appropriate bridges, controllers, and/or adapters. Also coupled to the bus system 28 are a display device (including an appropriate display controller) 24, which may be a cathode ray tube (CRT), liquid crystal display (LCD), or the like; a keyboard 25; a pointing device 26, such as a mouse, trackball, touchpad, or the like; a communication device 27; and a printer 29. Communication device 27 may be used to communicate the data and control signals to and/or from the detectors 10 and/or other computer systems or components. Communication device 27 may be, for example, a simple transceiver, a network adapter, a modem, or any other suitable data communication device. Display device 24 and printer 29 may be used to display and print, respectively, tomographic images reconstructed by processing system 18.

Figure 3:
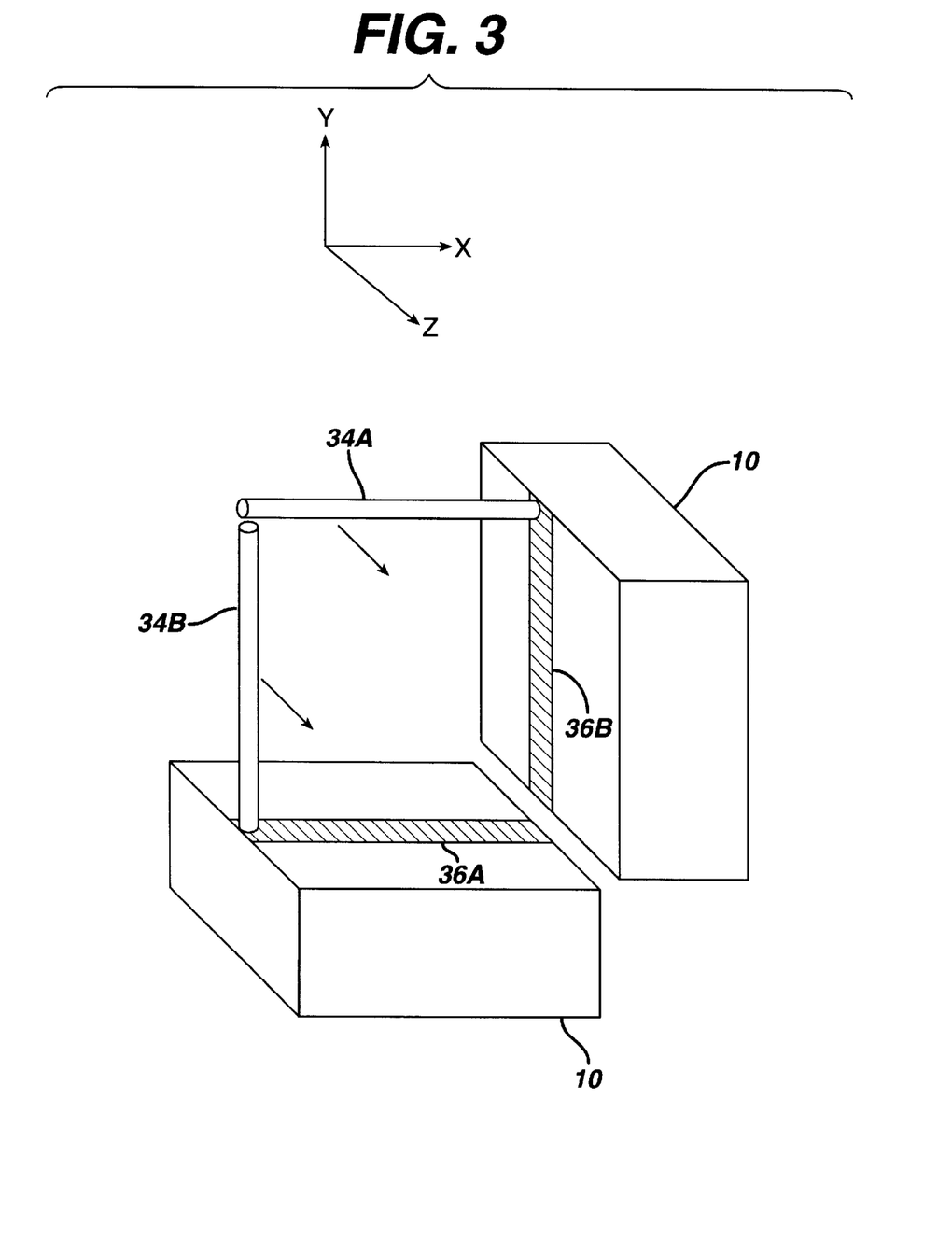
FIG. 3 illustrates two detectors and two radiation line sources in an arrangement for performing a transmission scan of a patient.

The illustrated imaging system corrects acquired emission data for the effects of attenuation using data acquired from a transmission scan of the patient (i.e., from an attenuation map of the patient). The transmission scan is performed using the line sources 34. As noted above, the line sources 34 are mounted to the gantry and a conventional manner, such that they are movable in translation along the z axis, relative to the detectors and the patient. The manner in which the line sources are physically coupled to the imaging system is not germane to the present invention and is therefore not described herein. FIG. 3 illustrates an example of an arrangement of the line sources and the detectors which may be used to perform a transmission scan of the patient. As shown, the detectors 10 are arranged so that are imaging surfaces are perpendicular to each other. Line source 34A is positioned to transmit radiation to a corresponding transmission detection window 36A defined electronically on the imaging surface of one of the detectors 10, while line source 34B is positioned to transmit radiation to a corresponding transmission detection window 36B defined electronically on the other one of the detectors 10. To perform a standard transmission scan, the line sources 34A and 34B are each moved in translation along the z axis relative to the detectors and the patient, while transmitting radiation to the corresponding detector 10. Each transmission detection window 34A or 34B is moved along the imaging surface of the detector 10 in synchronization with the corresponding line source 34. This process is repeated with the line sources and detectors at various different angular positions about the axis of rotation. The data acquired at the various different angular positions forms an attenuation map, which is used to correct image data acquired during an emission scan of the patient. The emission scan may be performed concurrently with the transmission scan.

Figure 4:
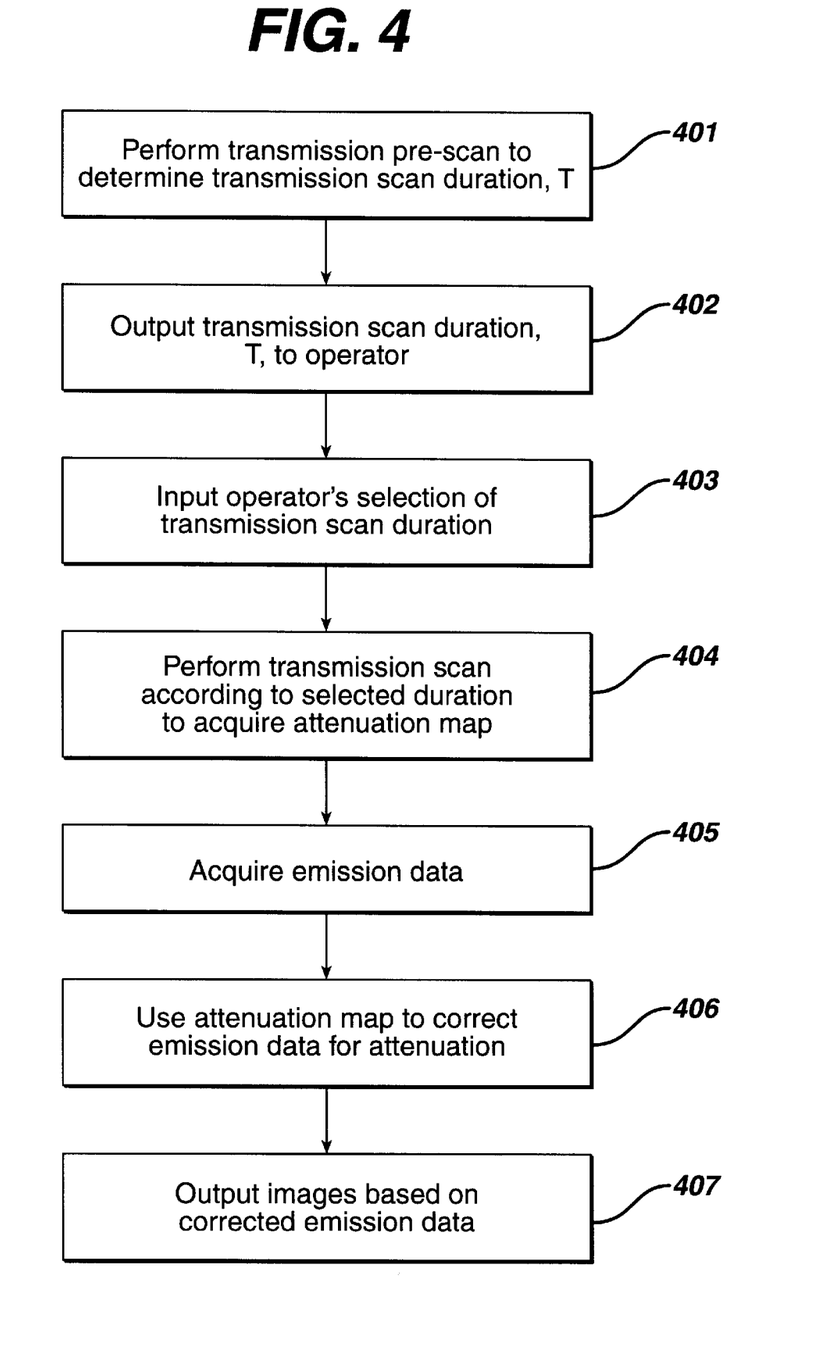
FIG. 4 is a flow diagram illustrating an overall procedure for generating attenuation-corrected images of patient.

As noted above, the described imaging system uses the results of a brief transmission pre-scan (e.g., 10 seconds), which is performed prior to the transmission scan, to compute to the desired duration of the transmission scan. FIG. 4 shows a procedure for generating attenuation-corrected images of patient, including the use of a transmission pre-scan. At 401, the transmission pre-scan of the patient is performed to determine a desired duration T of the transmission scan. At 402, the processing system 18 outputs the computed transmission scan duration T to the operator of the imaging system, which may be accomplished via the display device 24. The operator may accept this recommendation or reject it and manually enter a different transmission scan duration. Thus, at 403 the processing system 18 inputs the operator's selection of transmission scan duration, which may be a simple user input indicating the computed value T is accepted. The input may be received via the keyboard 25 or the pointing device 26, for example. At 404, the imaging system performs the transmission scan of the patient according to the selected transmission scan duration, to acquire an attenuation map of the patient. At 405, imaging system performs an emission scan of the patient to acquire emission data. Note that steps 404 and 405 may be performed concurrently. The processing system 18 then uses the attenuation map to correct the emission data for non-uniform attenuation at 406. At 407, the imaging system 18 outputs images of internal structures and/or functions of the patient's body, based on the attenuation-corrected emission data.

The manner in which the duration T of the transmission scan is computed will now be described in greater detail. According to one embodiment, the transmission pre-scan is performed for only a narrow sampling "slice" (set of z positions) of the patient, with the transmission source stationary. Thus, the pre-scan tends to expose the patient to less transmission radiation during the pre-scan than prior art transmission pre-scan techniques in which the transmission source is moved across the entire field of view of the detector. From the transmission pre-scan, a water-equivalent cross-section value of the patient is computed for the sampling slice. The transmission scan duration T is then computed based on the water-equivalent cross-section value and results of a reference scan. Use of the water-equivalent cross-section value is advantageous, because it is an objective measure of total attenuation presented in the sampled slice. Further, the water-equivalent cross-section value is independent of the pre-scan angle, i.e., it can be obtained from a pre-scan at any angle about the axis of rotation.

Figure 5:
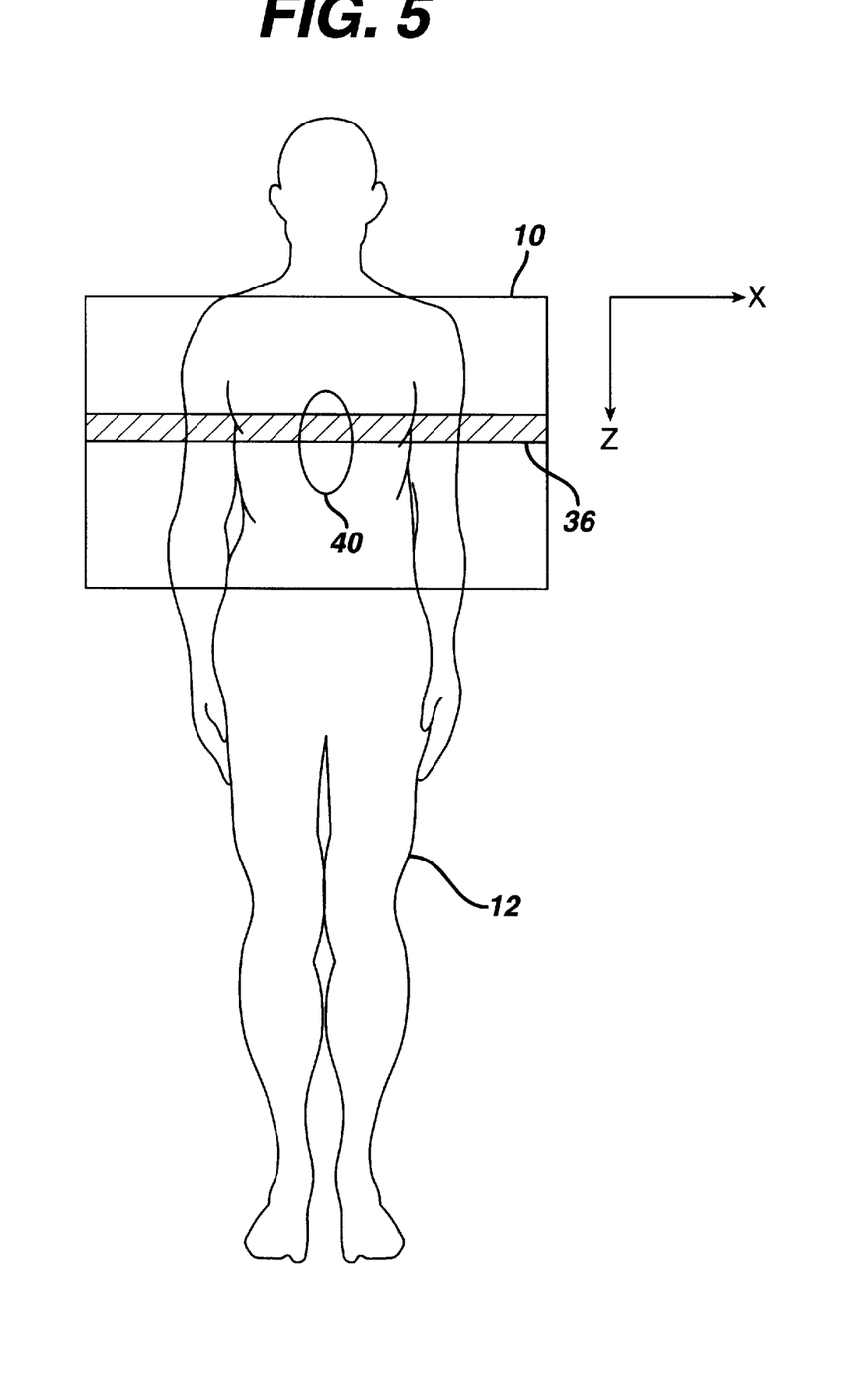
FIG. 5 illustrates the positioning of a transmission pre-scan window relative to a patient.

As shown in FIG. 5, the sampling slice 36 is chosen to intersect an organ of interest, such as the heart 40 in the case of a cardiac study, and is positioned at approximately the middle of the imaging surface of the detector 10. In contrast with at least one prior art technique, the line sources 34A and 34B are not scanned across the imaging surfaces of the detectors during the pre-scan, but are instead maintained in a fixed position along the z axis, such that only the sample slice 36 is used for the transmission pre-scan. Thus, the present pre-scan technique tends to reduce the transmission pre-scan radiation exposure in comparison to prior art transmission pre-scans which require movement of the transmission sources across the field of view of the detectors.

Consider now that at a transmission projection point j (where j represents either an x or y coordinate), the transmission counts with and without an object between a transmission source and a detector are represented by I(j) and $I_0(j)$ respectively. The relationship between I(j) and $I_0(j)$ can be represented by equation (1), where s represents pixel size (linear), and $\mu_{ij}$ represents the attenuation coefficient at point i along line j.

$$I(j) = I_0(j) e^{-s \sum_i \mu_{ji}} \quad (1)$$

Equation (1) can be rewritten as equation (2), where $a_j$ represents the total attenuation along line j.

$$a_j = s \sum_i \mu_{ji} = \ln\left[\frac{I_0(j)}{I(j)}\right] \quad (2)$$

Summing over j gives the total attenuation A along a line that passes through every pixel in the slice, as represented in equation (3).

$$A = \sum_j a_j \quad (3)$$

The water-equivalent cross-section value $C_{we}$ of the slice can be obtained as represented in equation (4), where $\mu_{H_2O}$ is the attenuation coefficient of water in units of inverse length, and $C_{we}$ is in units of area.

$$C_{we} = \frac{s \cdot A}{\mu_{H_2O}} = \frac{s}{\mu_{H_2O}} \sum_j \ln\left[\frac{I_0(j)}{I(j)}\right] \quad (4)$$

Note that $C_{we}$ should be constant with respect to scan angle for the sample slice. Therefore, $C_{we}$ can be obtained from the results of a single transmission pre-scan. $I_0(j)$ in the above equations can be derived from a reference scan, which is a blank scan (a scan with no object between either transmission source and either detector). Thus, the pixel value $I_r(j)$ of the reference scan at point j can be represented as shown in equation (5), where the reference scan includes movement of the line sources in translation along the z axis at a velocity v while transmitting radiation. In equation (5), F(j) represents the line integral of the line source flux along the direction perpendicular to the line source, and $l_r$ is the pixel size (linear) for the reference scan.

$$I_r(j) = \frac{F(j) \cdot l_r}{v} \quad (5)$$

The relationship between $I_0(j)$ and F(j) can be represented according to equation (6), where $l_p$ is the pixel size (linear) for the transmission pre-scan, and $t_p$ is the duration of the transmission pre-scan.

$$I_0(j) = F(j) \cdot l_p \cdot t_p \quad (6)$$

Therefore, $I_0(j)$ can be determined based on the reference scan in accordance with equation (7). Note that $I_0(j)$ is a line integral along the line source traveling direction (z) in the reference scan. Therefore, I(j) should also be a line integral when calculating the water-equivalent cross-section value $C_{we}$.

$$I_0(j) = \frac{I_r(j) \cdot v \cdot l_p \cdot t_p}{l_r} \quad (7)$$

The desired transmission scan time T can be estimated from $C_{we}$, the duration $t_{ref}$ of the reference scan, the mean pixel value $g_{ref}$ of the reference scan image, and a minimum desired transmission scan count $g_{min}$ (which is based on desired transmission image quality), as set forth in equation (8). The estimation represented by equation (8) is based on the assumption that the sample slice can be represented as an elliptical cylinder filled with water.

$$T = \frac{t_{ref} \cdot g_{min}}{g_{ref}} e^{d \cdot \mu_{H_2O}} \quad (8)$$

The parameter d in equation (8) is a function of $C_{we}$ and is defined by equation (9), where r is the ratio of the long axis to the short axis of the elliptical cylinder.

$$d = \sqrt{\frac{4r \cdot C_{we}}{\pi}} \qquad (9)$$

Figure 6:
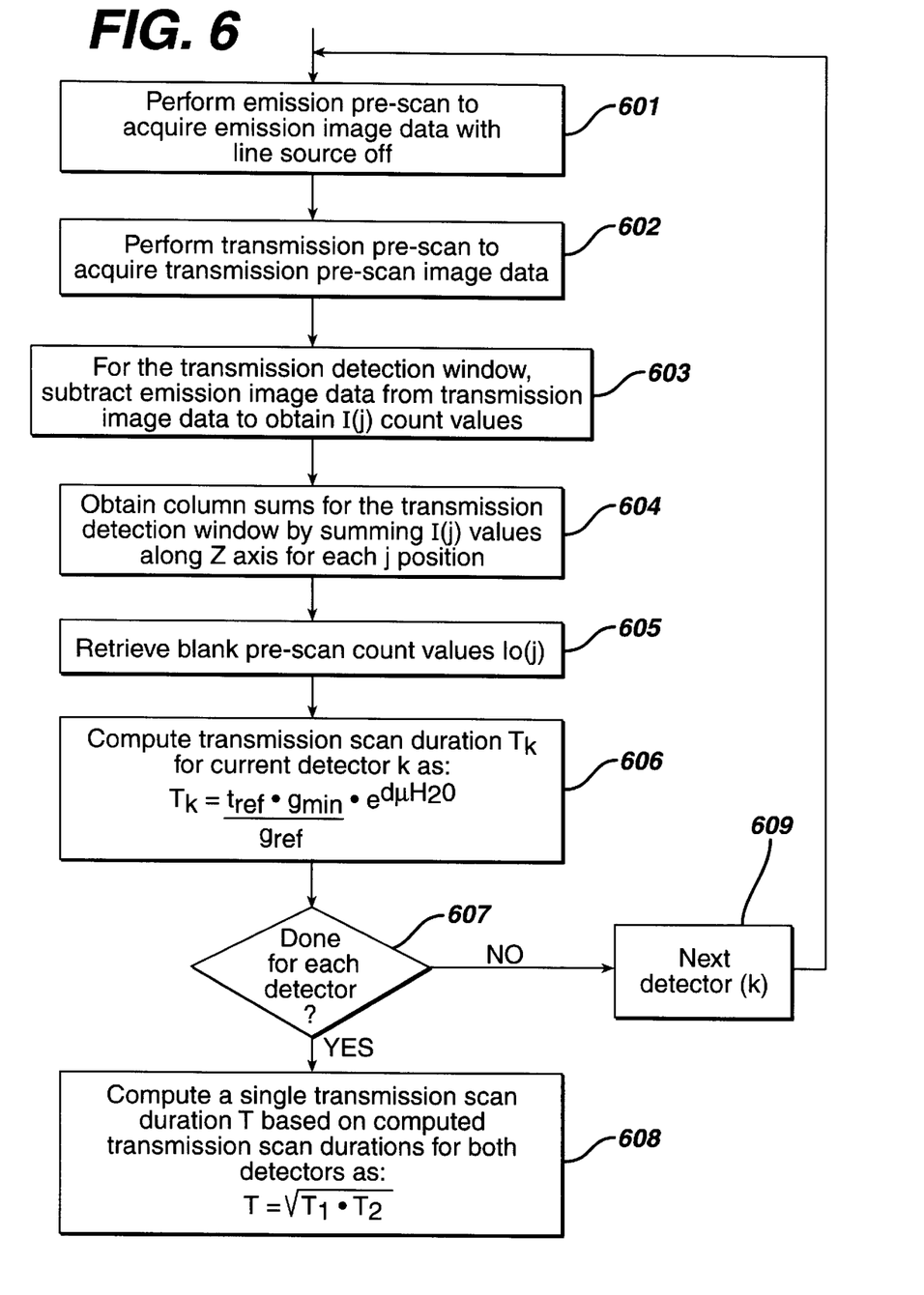
FIG. 6 is a flow diagram illustrating an overall procedure for using a transmission pre-scan to compute the duration of a subsequent transmission scan, based on a reference scan and a water-equivalent cross-section value.

Refer now to FIG. 6, which illustrates in greater detail the step 401 of computing the duration T of the transmission scan based on a transmission pre-scan. The procedure of FIG. 6 is based on the assumption that the $I_0(j)$ values have been previously computed, based on a previously performed reference scan, and have been stored in a readily accessible data file (e.g., in mass storage device 23). Reference scans may be performed on a daily basis, for example, prior to operating the imaging system with a patient. It may also be desirable to perform a separate reference scan for each collimator that can be used on the detectors 10; hence a separate file may be created for the $I_0(j)$ values for each such collimator.

It is also assumed that both the transmission pre-scan and the transmission scan itself are performed after patient has been injected with the radiopharmaceutical. Accordingly, the described procedure includes a correction for emission contamination in the transmission pre-scan data. Specifically, for given detector, at 601 an emission pre-scan is performed using the transmission energy acceptance range to acquire emission pre-scan data, with the line sources off. Only emission data acquired within the sample window 36 (see FIG. 5) is required, although data may be acquired for the entire imaging surface of the detector 10 if desired. At 602, the appropriate line source is operated to perform the transmission pre-scan, resulting in the acquisition of transmission pre-scan image data for the sample window 36. As noted, the transmission pre-scan may be very brief (e.g., 10 seconds) and is performed with the line source stationery with respect to the z axis. At 603, the emission pre-scan data is subtracted from the transmission pre-scan data for the sample window 36, to obtain the transmission pre-scan I(j) values. At 604, the count values I(j) for each position j are integrated along z, to form a single count value (a "column sum") for each position j. This integration is performed to relate the duration of the transmission scan, in which the line source is moved axially across the field of view of the detector, to the pre-scan, in which the line source fixed. (Note that the beam width of the line source in the line source travelling direction, z, is wider than a single pixel. The entire beam can be divided into pixels indexed by j in the direction parallel to the line source, i.e., x or y. During a transmission scan with a moving line source, a pixel in the transmission projection receives contributions from all pixels in the beam that have the same index j.) At 605, the $I_0(j)$ values are retrieved from the appropriate file based on the collimator that is being used. At 606, a transmission scan duration $T_k$ for the current detector (where k=1 or 2 for a two-detector system), is computed as set forth in equation (8). The foregoing procedure is then repeated for each remaining detector (607, 609). Alternatively, the foregoing procedure may be performed concurrently for both detectors using their corresponding line sources. The final transmission scan duration T is computed at 608 as a function of the computed transmission scan durations $T_1$ and $T_2$ for the two detectors, as set forth in equation (10).

$$T = \sqrt{T_1 \cdot T_2} \qquad (10)$$

An alternative method for using a transmission pre-scan to compute transmission scan duration T will now be described. This alternative method does not rely upon computation of a water-equivalent cross-section value or the availability of reference scan data. In this alternative method, the transmission scan duration is estimated based on the number of counts collected in the least-penetrated portion of the sampling slice of the transmission pre-scan. Accordingly, this alternative method may be easier to implement under certain circumstances.

In the alternative method, the transmission scan duration T is computed according to equation (11), where R is the total distance traveled by the line source along the z axis during a normal transmission scan; $I_{min}$ is the minimum mean desired number of counts per pixel for the transmission image (based on desired quality); s is the transmission scan image pixel size; $t_p$ is the duration of the transmission pre-scan; and, m is the computed mean number of counts for those pixels in a specified lowest percentile of the pixels in the sample window. It is assumed that both the matrix size and the zoom are the same for the pre-scan and the transmission scan.

$$T = \frac{R \cdot I_{min}}{s \cdot m} \cdot t_p \qquad (11)$$

Figure 8:
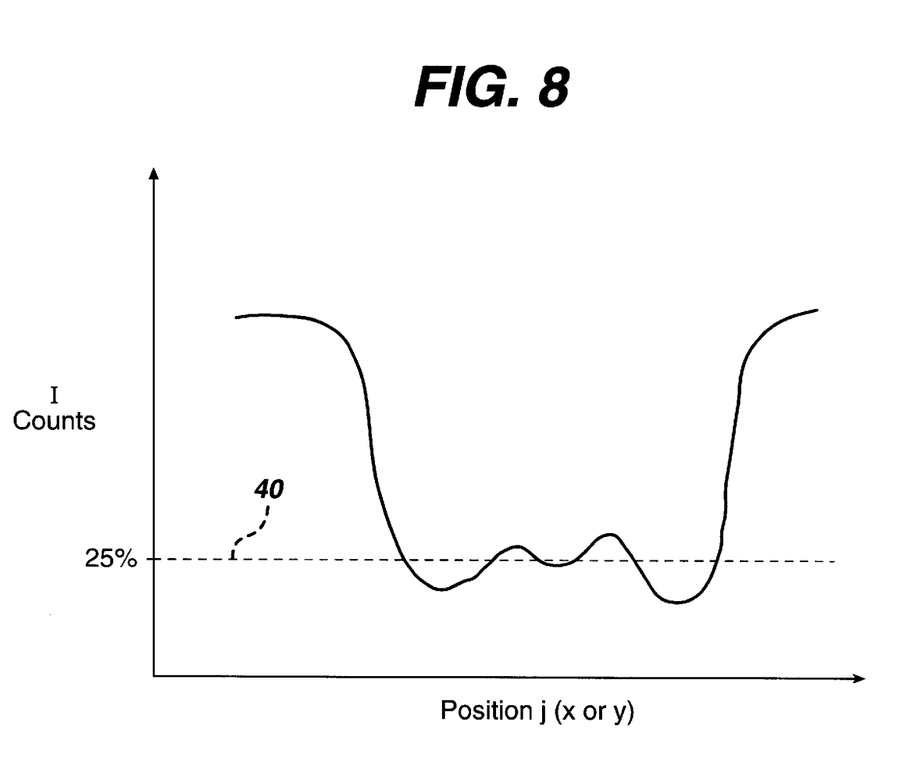
FIG. 8 shows and example of a projection that may result from a transmission pre-scan for a sample slice.

The computation of the value m is now explained further with reference to FIG. 8. FIG. 8 shows an example of a projection that may result from a transmission pre-scan for the sample window 36. The projection represents count values I with respect to position j (where j represents either the x or y axis). As shown, the center of the projection corresponds to the middle of the body and, therefore, to greater thicknesses of tissue in the path of the radiation. Consequently, the measured count values I tend to be lower near the center of the projection, since there is greater attenuation. Conversely, the measured count values I tend to be higher near the edges of the projection, which correspond to the edges of the body and smaller thickness of tissue in the path of the radiation.

To acquire the projection for the sample window 36, the count values I for each position j are integrated along z, to form a single count value I (a "column sum") for each position j. As explained above, this integration is used in order to relate the duration of the transmission scan, which is performed with a moving line source, to the pre-scan, which is performed with the line source fixed. The value m is then computed as the mean of the column sums in a predetermined lowest percentile, such as the lowest 25 percent of column sums (e.g., those count values falling below line 40 in FIG. 8).

Figure 7:
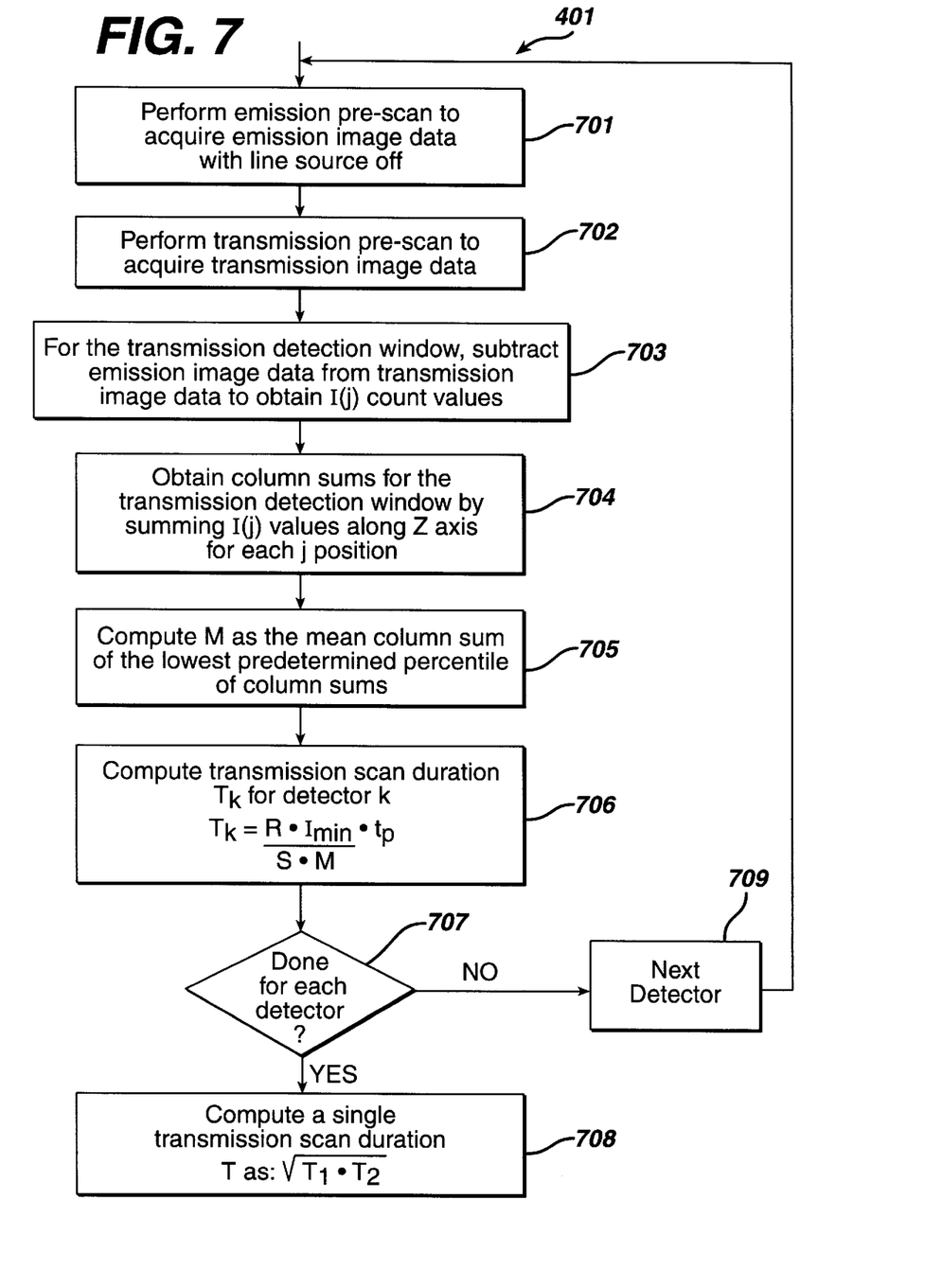
FIG. 7 is a flow diagram illustrating an overall procedure for using a transmission pre-scan to compute the duration of a subsequent transmission scan without the use of a reference scan.

Refer now to FIG. 7, which shows a procedure for computing the transmission scan duration T in accordance with this alternative method. At 701, for a given detector, an emission pre-scan is performed using the transmission energy acceptance range to acquire emission pre-scan data, with the line sources off. Only data acquired within the sample window 36 is required, although data may be acquired for the entire imaging surface of the detector 10 if desired. At 702, the appropriate line source is operated to perform the transmission pre-scan, resulting in the acquisition of transmission pre-scan image data for the sample window 36 (FIG. 5). Again, the transmission pre-scan may be very brief (e.g., 10 seconds) and is performed with the line source stationery with respect to the z axis. At 703, the emission pre-scan data is subtracted from the transmission pre-scan data for the sample window 36, to obtain the transmission pre-scan I(j) values. At 704, the resulting I(j) values are integrated along z for each j position to obtain a number of column sums, one column sum for each j position. Next, the value m is computed as the mean column sum of a predetermined lowest percentile of the column sums at 705. It may be desirable to exclude columns sums corresponding to positions outside the field of view of the detector for purposes of computing m. The transmission scan duration $T_k$ for the current detector, detector k, is then computed according to equation (11). The foregoing steps are also performed for each additional detector (707, 709). At 707, the final transmission scan duration T is computed as a function of the computed transmission scan durations $T_1$ and $T_2$ of the two detectors, as set forth in equation (10).

Thus, a method and apparatus for performing a transmission pre-scan of a patient using a nuclear medicine imaging system, to determine the duration of a subsequent transmission scan of the patient have been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative sense rather than a restrictive sense.

What is claimed is:

1. A method of determining a duration of a transmission scan of an object to be imaged, the method comprising:
   using a radiation transmission source and a radiation detector to perform a transmission pre-scan of the object;
   determining a water-equivalent cross-section value of the object based on data acquired from the transmission pre-scan; and
   computing the duration of the transmission scan based on the water-equivalent cross-section value.

2. A method as recited in claim 1, wherein said determining the water-equivalent cross-section value of the object comprises using data based on a blank transmission scan and the data acquired from the transmission pre-scan to determine the water-equivalent cross-section value.

3. A method as recited in claim 2, wherein said determining the water-equivalent cross-section value of the object further comprises determining the water-equivalent cross-section value $C_{we}$ based on the formula $C_{we}=(s/\mu_{H2O})\Sigma_j(\ln(I_0(j)/I(j)))$, wherein
   s represents pixel size;
   $\mu_{H2O}$ represents the attenuation coefficient of water;
   j is a positional index;
   $I_0(j)$ represents a count value based on the blank transmission scan; and
   I(j) represents a count value of the transmission pre-scan.

4. A method as recited in claim 1, wherein said computing the duration of the transmission scan based on the water-equivalent cross-section value comprises computing the duration T of the transmission scan based on the formula $T=((t_{ref}\,g_{min})/g_{ref})e^{d\mu H2O}$, wherein
   $t_{ref}$ represents the duration of a blank transmission scan;
   $g_{min}$ represents a minimum transmission scan count value;
   $g_{ref}$ represents a count value based on the blank transmission scan;
   d is a function of the water-equivalent cross-section value; and
   $\mu_{H2O}$ represents the attenuation coefficient of water.

5. A method as recited in claim 4, wherein said determining the water-equivalent cross-section value of the object further comprises determining the water-equivalent cross-section value $C_{we}$ based on the formula $C_{we}=(s/\mu_{H2O})\Sigma_j\ln(I_0(j)/I(j))$,
   s represents pixel size;
   j is a positional index value;
   $I_0(j)$ represents a count value based on the blank transmission scan; and
   I(j) represents a count value of the transmission pre-scan.

6. A method as recited in claim 1, further comprising correcting the data acquired from the transmission pre-scan for emission contamination prior to said determining the water-equivalent cross-section value of the object.

7. A method as recited in claim 1, wherein the radiation transmission source remains stationary during the transmission pre-scan.

8. A method as recited in claim 1, further comprising:
   using the radiation transmission source and the detector to perform the transmission scan according to said determined duration; and
   using data acquired from the transmission scan to correct emission data of the object for attenuation.

9. In a medical imaging system, a method of determining a duration of a transmission scan of an object to be imaged, the transmission scan for acquiring attenuation correction data of the object, the method comprising:
   using a radiation transmission source and a radiation detector of the medical imaging system to perform a transmission pre-scan of the object, the transmission pre-scan having a duration less than the duration of the transmission scan;
   determining a water-equivalent cross-section value of the object based on data acquired from the transmission pre-scan and data based on a blank transmission scan; and
   computing the duration T of the transmission scan based on the formula $$T=((t_{ref}\,g_{min})/g_{ref})e^{d\mu H2O},$$

wherein
   $t_{ref}$ represents the duration of the blank transmission scan,
   $g_{min}$ represents a minimum desired transmission scan count value,
   $g_{ref}$ represents a count value based on the blank transmission scan,
   d is a function of the water-equivalent cross-section value, and
   $\mu_{H2O}$ represents the attenuation coefficient of water.

10. A method as recited in claim 9, further comprising correcting the data acquired from the transmission pre-scan for emission contamination prior to said determining the water-equivalent cross-section value of the object.

11. A method as recited in claim 9, wherein the radiation transmission source remains stationary relative to a long axis of the object during the transmission pre-scan.

12. A method as recited in claim 9, wherein said determining the water-equivalent cross-section value of the object comprises determining the water-equivalent cross-section value $C_{we}$ of the object based on the $C_{we}=(s/\mu_{H2O})\Sigma_j\ln(j)/I(j))$, wherein
   s represents pixel size;
   $\mu_{H2O}$ represents the attenuation coefficient of water;
   j is a positional index value;
   $I_0(j)$ represents a count value based on the blank transmission scan; and
   I(j) represents a count value of the transmission pre-scan.

13. A method as recited in claim 9, further comprising:

using the radiation transmission source and the radiation detector to perform the blank transmission scan, including moving the radiation transmission source in translation while transmitting radiation to the detector;

acquiring a plurality of count values $I_r$ from the blank transmission scan; and computing a plurality of count values $I_0$ based on the $I_r$ values, such that said $I_0$ values represent a blank transmission scan with a stationary transmission source.

14. A method as recited in claim 9, further comprising:

using the radiation transmission source and the detector to perform the transmission scan according to said determined duration; and using data acquired from the transmission scan to correct emission data of the object for attenuation.

15. In a nuclear medicine imaging system, a method of determining a duration of a transmission scan of an object to be imaged, the transmission scan for acquiring attenuation correction data of the object, the method comprising:

using a radiation transmission source and a radiation detector of the nuclear medicine imaging system to perform a transmission pre-scan of the object, the transmission pre-scan having a duration less than the duration of the transmission scan, wherein the radiation transmission source remains stationary during the transmission pre-scan;

correcting data acquired from the transmission pre-scan for emission contamination;

determining a water-equivalent cross-section value $C_{we}$ of the object based on the data acquired from the transmission pre-scan and data based on a blank transmission scan, based on the formula $C_{we}=(s/\mu_{H2O})\Sigma_j \ln(I_0(j)/I(j))$, wherein s represents pixel size, $\mu_{H2O}$ represents the attenuation coefficient of water, j is a positional index value, $I_0(j)$ represents a count value based on the blank transmission scan, and $I(j)$ represents a count value of the transmission pre-scan; and computing the duration T of the transmission scan based on the formula $$T=((t_{ref} g_{min})/g_{ref})e^{d\mu_{H2O}},$$

wherein $t_{ref}$ represents the duration of a blank transmission scan, $g_{min}$ represents a minimum transmission scan count value, $g_{ref}$ represents a count value based on the blank transmission scan, and d is a function of the water-equivalent cross-section value.

16. A method as recited in claim 15, further comprising:

using the radiation transmission source and the radiation detector to perform the blank transmission scan, including moving the radiation transmission source in translation while transmitting radiation to the detector;

acquiring a plurality of count values $I_r(j)$ from the blank transmission scan; and computing said $I_0(j)$ values based on the $I_r(j)$ values, such that said $I_0(j)$ values represent a blank transmission scan with a stationary transmission source.

17. A nuclear medicine imaging system comprising:

a radiation transmission source;

a radiation detector;

means for controlling the radiation transmission source and the radiation detector to perform a transmission pre-scan of an object to be imaged;

means for determining a water-equivalent cross-section value of the object based on data acquired from the transmission pre-scan;

means for computing a duration of a transmission scan based on the water-equivalent cross-section value;

means for controlling the radiation transmission source and the detector to perform the transmission scan according to said determined duration to acquire attenuation data of the object;

means for controlling the detector to perform an emission scan of the object to acquire emission data of the object; and means for using the attenuation data to correct the emission data of the object for attenuation; and means for generating images of the object based on the attenuation-corrected emission data.

18. A nuclear medicine imaging system as recited in claim 17, wherein said means for determining the water-equivalent cross-section value of the object comprises means for using data based on a blank transmission scan and the data acquired from the transmission pre-scan to determine the water-equivalent cross-section value.

19. A nuclear medicine imaging system as recited in claim 18, wherein said means for determining the water-equivalent cross-section value of the object further comprises means for determining the water-equivalent cross-section value $C_{we}$ based on the formula $C_{we}=(s/\mu_{H2O})\Sigma_j \ln(I_0(j)/I(j))$, wherein s represents pixel size;

$\mu_{H2O}$ represents the attenuation coefficient of water;

j is a positional index value;

$I_0(j)$ represents a count value based on the blank transmission scan; and $I(j)$ represents a count value of the transmission pre-scan.

20. A nuclear medicine imaging system as recited in claim 17, wherein said means for computing the duration of the transmission scan based on the water-equivalent cross-section value comprises means for computing the duration T of the transmission scan based on the formula $T=((t_{ref} g_{min})/g_{ref})e^{d\mu_{H2O}}$, wherein $t_{ref}$ represents the duration of a blank transmission scan;

$g_{min}$ represents a minimum transmission scan count value;

$g_{ref}$ represents a count value based on the blank transmission scan;

d is a function of the water-equivalent cross-section value; and $\mu_{H2O}$ represents the attenuation coefficient of water.

21. A nuclear medicine imaging system as recited in claim 20, wherein said means for determining the water-equivalent cross-section value of the object further comprises means for determining the water-equivalent cross-section value $C_{we}$ based on the formula $C_{we}=(s/\mu_{H2O})\Sigma_j \ln(I_0(j)/I(j))$, wherein s represents pixel size;

j is a positional index value;

$I_0(j)$ represents a count value based on the blank transmission scan; and $I(j)$ represents a count value of the transmission pre-scan.

22. A nuclear medicine imaging system as recited in claim 17, further comprising means for correcting the data acquired from the transmission pre-scan for emission contamination prior to said determining the water-equivalent cross-section value of the object.

23. A nuclear medicine imaging system as recited in claim 17, wherein the radiation transmission source remains stationary during the transmission pre-scan.

24. A nuclear medicine imaging system as recited in claim 17, further comprising:
means for using the radiation transmission source and the detector to perform the transmission scan according to said determined duration; and
means for using data acquired from the transmission scan to correct emission data of the object for attenuation.

25. A gamma camera imaging system comprising:
a plurality of radiation detectors;
a plurality of radiation transmission line sources;
a gantry rotatably supporting the detectors and the line sources;
a processing system configured to:
control at least one of the line sources and at least one of the detectors to perform a transmission pre-scan of the object;
determine a water-equivalent cross-section value of the object based on data acquired from the transmission pre-scan and data based on a blank transmission scan;
compute a duration for a transmission scan based on the water-equivalent cross-section value; and
control at least one of the line sources and at least one of the detectors to perform the transmission scan of the object, based on the determined duration.

26. A gamma camera imaging system as recited in claim 25, wherein the processing system is further configured to:
control the detectors to acquire emission data of the object;
correct the emission data for attenuation based on data acquired from the transmission scan; and
generate images of the object based on the attenuation-corrected emission data.

27. A gamma camera imaging system as recited in claim 25, wherein the processing system is configured to compute the duration T of the transmission scan based on the formula $$T=((t_{ref}\, g_{min})/g_{ref})e^{d\mu H2O},$$

wherein
$t_{ref}$ represents the duration of the blank transmission scan,
$g_{min}$ represents a minimum desired transmission scan count value,
$g_{ref}$ represents a count value based on the blank transmission scan, and
d is a function of the water-equivalent cross-section value.

28. A gamma camera imaging system as recited in claim 25, wherein the processing system is configured to determine the water-equivalent cross-section value $C_{we}$ of the object based on the formula $C_{we}=(s/\mu_{H2O})\Sigma_j \ln(I_0(j)/I(j))$, wherein
s represents pixel size;
$\mu_{H2O}$ represents the attenuation coefficient of water;
j is a positional index value;
$I_0(j)$ represents a count value based on the blank transmission scan; and
I(j) represents a count value of the transmission pre-scan.

29. A gamma camera imaging system as recited in claim 25, wherein the processing system is configured to correct the data acquired from the transmission pre-scan for emission contamination prior to determining the water-equivalent cross-section value of the object.

30. A gamma camera imaging system as recited in claim 25, wherein the radiation transmission source remains stationary during the transmission pre-scan.

31. A gamma camera imaging system as recited in claim 25, wherein the processing system is configured to:
control at least one of the line sources and at least one of the detectors to perform the blank transmission scan, including moving said at least one of the line sources in translation while transmitting radiation said at least one of the detectors;
acquiring a plurality of count values $I_r$ from the blank transmission scan; and
computing a plurality of count values $I_0$ based on the $I^r$ values, such that said $I_0$ values represent a blank transmission scan with a stationary line source.

32. In a gamma camera imaging system, a method of determining the duration of a transmission scan of an object to be imaged, the method comprising:
using a radiation transmission source and a radiation detector to perform a transmission pre-scan of the object;
acquiring transmission pre-scan data of the object based on the transmission pre-scan, the transmission pre-scan data including a plurality of count values, each count value associated with one of a plurality of positions along a first axis;
selecting a subset of the count values based on the count values;
computing a value corresponding to an average of the subset of the count values; and
computing the duration of the transmission scan based on the value and the duration of the transmission pre-scan.

33. A method as recited in claim 32, wherein said selecting a subset of the count values comprises identifying a predetermined lowest percentile of the count values.

34. A method as recited in claim 32, wherein the radiation transmission source remains stationary during the transmission pre-scan.

35. A method as recited in claim 32, wherein each of the count values of the transmission pre-scan data represents, for a corresponding position along the first axis, an integration of count values along a second axis perpendicular to the first axis.

36. A method as recited in claim 32, further comprising correcting the transmission pre-scan data for emission contamination prior to said selecting the subset of count values.

37. In a gamma camera imaging system, a method of determining the duration of a transmission scan of an object to be imaged, the method comprising:
using a radiation transmission source and a radiation detector to perform a transmission pre-scan of the object, wherein the radiation transmission source remains stationary during the transmission pre-scan;
acquiring transmission pre-scan data of the object based on the transmission pre-scan, the transmission pre-scan data including a plurality of count values, each count value associated with one of a plurality of positions along a first axis, wherein each of the count values of the transmission pre-scan data represents, for a corresponding position along the first axis, an integration of count values along a second axis perpendicular to the first axis;

correcting the transmission pre-scan data for emission contamination;

selecting a subset of the count values by identifying a predetermined lowest percentile of the count values;

computing a value corresponding to an average of the subset of the count values; and computing the duration of the transmission scan based on the value and the duration of the transmission pre-scan.

38. A medical imaging system comprising:

a radiation source;

a radiation detector;

means for controlling the radiation source and the radiation detector to perform a transmission pre-scan of an object to be imaged;

means for acquiring transmission pre-scan data of the object based on the transmission pre-scan, the transmission pre-scan data including a plurality of count values, each count value associated with one of a plurality of positions along a first axis;

means for selecting a subset of the count values based on the count values;

means for computing a value corresponding to an average of the subset of the count values; and means for computing the duration of the transmission scan based on the value and the duration of the transmission pre-scan.

39. A medical imaging system as recited in claim 38, wherein said means for selecting a subset of the count values comprises means for identifying a predetermined lowest percentile of the count values.

40. A medical imaging system as recited in claim 38, wherein the radiation source remains stationary during the transmission pre-scan.

41. A medical imaging system as recited in claim 38, wherein each of the count values of the transmission pre-scan data represents, for a corresponding position along the first axis, an integration of count values along a second axis perpendicular to the first axis.

42. A medical imaging system as recited in claim 38, further comprising means for correcting the transmission pre-scan data for emission contamination prior to said selecting the subset of count values.

\* \* \* \* \*

UNITED STATES PATENT AND TRADEMARK OFFICE
CERTIFICATE OF CORRECTION

PATENT NO. : 6,259,097 B1
DATED : July 10, 2001
INVENTOR(S) : Lingxiong Shao, Jingham Ye and Soo Kuen Hom It is certified that error appears in the above-identified patent and that said Letters Patent is hereby corrected as shown below:

Column 10,
Line 60, "$\Sigma_j \ln(j)/I(j))$" should be -- $\Sigma_j \ln(I_0(j)/I(j))$ --

Column 14,
Line 17, "I'" should be -- $I_r$ --

Signed and Sealed this

Thirtieth Day of April, 2002

Attest:

Attesting Officer

JAMES E. ROGAN
Director of the United States Patent and Trademark Office